(12) United States Patent
Saito et al.

(10) Patent No.: US 10,508,909 B2
(45) Date of Patent: Dec. 17, 2019

(54) LINE DISPLACEMENT EVALUATION METHOD, LINE DISPLACEMENT EVALUATION DEVICE, PROGRAM, AND RECORDING MEDIUM

(71) Applicant: NIPPON STEEL & SUMITOMO METAL CORPORATION, Tokyo (JP)

(72) Inventors: Masahiro Saito, Futtsu (JP); Tohru Yoshida, Chiba (JP)

(73) Assignee: NIPPON STEEL CORPORATION, Tokyo (JP)

( * ) Notice: Subject to any disclaimer, the term of this patent is extended or adjusted under 35 U.S.C. 154(b) by 193 days.

(21) Appl. No.: 15/502,030

(22) PCT Filed: Aug. 6, 2015

(86) PCT No.: PCT/JP2015/072354
§ 371 (c)(1),
(2) Date: Feb. 6, 2017

(87) PCT Pub. No.: WO2016/021685
PCT Pub. Date: Feb. 11, 2016

(65) Prior Publication Data
US 2017/0227356 A1    Aug. 10, 2017

(30) Foreign Application Priority Data
Aug. 8, 2014  (JP) ................. 2014-163022

(51) Int. Cl.
*G01B 21/20* (2006.01)
*B21D 22/26* (2006.01)
(Continued)

(52) U.S. Cl.
CPC ............. *G01B 21/20* (2013.01); *B21D 22/00* (2013.01); *B21D 22/26* (2013.01); *B21D 53/88* (2013.01);
(Continued)

(58) Field of Classification Search
CPC ........ G01B 21/20; B21D 22/00; B21D 22/26; B21D 5/88; B01B 11/24; G06T 17/30; G01N 21/9515; G01N 2021/8883
See application file for complete search history.

(56) References Cited

U.S. PATENT DOCUMENTS 7,869,061 B2 *  1/2011  Sato ................... G01B 11/2536
                                                        356/603
8,429,946 B2 *  4/2013  Maeda .................. B21D 22/02
                                                          72/350

(Continued)

FOREIGN PATENT DOCUMENTS

| CN | 101356418 A | 1/2009 |
|----|-------------|--------|
| CN | 102667939 A | 9/2012 |

(Continued)

OTHER PUBLICATIONS

Chapter 9 Defection of Beams, https://web.archive.org/web/20130903025435/http://ocw.nthu.edu.tw/ocw/upload/8/258/Chapter_9-98.pdf accessed on Oct. 11, 2018, document published online Sep. 3, 2013.*

(Continued)

*Primary Examiner* — Mohamed Charioui
*Assistant Examiner* — Catherine T. Rastovski
(74) *Attorney, Agent, or Firm* — Birch, Stewart, Kolasch & Birch, LLP

(57) ABSTRACT

Provided is a line displacement evaluation method of evaluating line displacement occurring in a press-formed article in press forming of forming a character line. This method includes acquiring a cross section profile of the press-formed article measured so as to traverse the character line formed in the press-formed article; calculating a 4th order differential coefficient of the acquired cross section profile; and evaluating the line displacement, on the basis of the calcu- (Continued)

lated 4th order differential coefficient of the cross section profile.

12 Claims, 7 Drawing Sheets

(51) Int. Cl.
*G01B 11/24* (2006.01)
*G06T 17/30* (2006.01)
*B21D 22/00* (2006.01)
*B21D 53/88* (2006.01)
*G01N 21/95* (2006.01)
*G01N 21/88* (2006.01)

(52) U.S. Cl.
CPC .............. *G01B 11/24* (2013.01); *G06T 17/30* (2013.01); *G01N 21/9515* (2013.01); *G01N 2021/8883* (2013.01)

(56) References Cited

U.S. PATENT DOCUMENTS

| | | | | |
|---|---|---|---|---|
| 9,003,846 | B2 * | 4/2015 | Isei | ........................ B21C 51/00 72/11.2 |
| 9,962,752 | B2 * | 5/2018 | Uchiyama | ............... B21D 22/21 |
| 2015/0186554 | A1 * | 7/2015 | Saito | ................... G06F 17/5018 703/1 |

FOREIGN PATENT DOCUMENTS

| | | |
|---|---|---|
| CN | 103604599 A | 2/2014 |
| JP | 2007-127610 A | 5/2007 |
| JP | 4957291 B2 | 6/2012 |
| JP | 5387491 B2 | 1/2014 |
| RU | 2393426 C2 | 6/2010 |
| RU | 2517149 C2 | 5/2014 |
| SU | 1151815 A | 4/1985 |
| SU | 1763863 A1 | 9/1992 |

OTHER PUBLICATIONS

Biorentino et al., "Automatic image-based car profile character line recognition", Proceeding of the IMProVe 2011 International conference on Innovation Methods in Product Design, Jun. 3, 15-17, 2011, Venice, Italy.*

Written Opinion of the International Searching Authonty for PCT/JP2015/072354 (PCT/ISA/237) dated Nov. 2, 2015.

Russian Office Action and Search Report for counterpart Russian Application No. 2017104996, dated Mar. 12, 2018, with English translations.

Chinese Office Action and Search Report for counterpart Chinese Application No. 201580042215.2, dated Aug. 1, 2018, with English translation of the Search Report.

Aga et al., "Optimization of Die Design Based on Statistical Analysis of Forming Defect", Kata Gijutsu, Jul. 1, 1998, vol. 13, No. 8, pp. 130-131, total 3 pages.

International Search Report for PCT/JP2015/072354 dated Nov. 2, 2015.

Nakano et al., "Innovation in Body Production for New Axela", Mazda technical review, 2013, No. 31, pp. 38-43, total 8 pages.

Written Opinion of the International Searching Authority for PCT/JP2015/072354 (PCT/ISA/237) dated Nov. 2, 2015.

* cited by examiner

LINE DISPLACEMENT EVALUATION METHOD, LINE DISPLACEMENT EVALUATION DEVICE, PROGRAM, AND RECORDING MEDIUM

TECHNICAL FIELD

The present invention relates to a line displacement evaluation method, a line displacement evaluation device, a program, and a recording medium. More specifically, the present invention relates to a line displacement evaluation method, a line displacement evaluation device, a program, and a recording medium that evaluate line displacement occurring in a press-formed article in press forming of forming a character line.

Priority is claimed on Japanese Patent Application No. 2014-163022, filed Aug. 8, 2014, the content of which is incorporated herein by reference.

BACKGROUND ART

In recent years, high designability are demanded for outer panels of automobiles. In order to satisfy such demands, a sharp character line may be formed on an outer panel. In order to realize a design at the time of designing, it is necessary to faithfully reproduce a surface adjacent to an R stop (a radius curve end or a boundary between a curve and a straight line) of a character line during press forming. However, an initial striking part between a stock plate in which a character line is formed, and a punch die protruding part may moves out of the R stop of the character line in a final product, depending on an amount by which the stock version, such as a steel sheet or an aluminum alloy plate, flows in from respective places of a crease suppressing part during press forming (positional displacement). As a result, a bending tendency remains in the external appearance of the outer panel in the vicinity of the initial striking part in the stock plate, irregularities remain outside the R stop of the character line after the press forming, and the external appearance quality of the outer panel is deteriorated. This is a line displacement (skid lines) phenomenon (see Non-Patent Document 1).

CITATION LIST

Patent Literature

Patent Document 1: Japanese Patent No. 5387491
Patent Document 2: Japanese Patent No. 4957291

Non-Patent Document

Non-Patent Document 1: Shinya Nakano, Akira Sakai, Yasuo Yamada: Mazda Technical Review, No. 31 (2013), Pages 38 to 43

SUMMARY OF INVENTION

Technical Problem

Under the present circumstances, the degree of the line displacement is determined by sensory evaluation of a worker on the spot. In a case where the degree of the line displacement is small, products may be shipped even if the line displacement occurs. The criterion of the line displacement is not clarified, and there is a concern that variations may occur in products.

As a technique of evaluating metal sheets after press forming, such as an outer panel, a technique of quantitatively evaluating surface deflection is disclosed in, for example, Patent Documents 1 and 2. However, the technique disclosed in Patent Documents 1 and 2 is not a technique of evaluating the line displacement.

A technique of measuring the surface shape of a metal sheet, calculating and filtering Gaussian curvature using values on orthogonal lattice points, and then evaluating surface deflection is disclosed in Patent Document 1. However, since it is difficult to distinguish the curvature of a panel shape that is present in a direction along a character line, and the curvature of a cross section change resulting from the line displacement, the Gaussian curvature of the surface shape of the metal sheet is unsuitable for catching the line displacement phenomenon.

A technique of imaging a plurality of light and dark patterns that move onto a surface to be measured to calculate surface deflection distribution, curvilinearly approximate the inclination of a surface calculated, and calculating the variation (secondary differential coefficient) of the inclination is disclosed in Patent Document 2. However, for example, in the case of a cross sectional shape (a cross sectional shape of a curved surface+a character line+curved surface) in which a character line was formed, for example on a curved surface, it is difficult to quantitatively evaluate the line displacement only with curvature distribution.

The invention has been made in view of the above points, and an object thereof is to allow line displacement occurring in a press-formed article in press forming of forming a character line to be quantitatively evaluated.

Solution to Problem

According to a first aspect of the invention, there is provided a line displacement evaluation method of evaluating line displacement occurring in a press-formed article in press forming of forming a character line. This method includes acquiring a cross section profile of the press-formed article measured so as to traverse the character line formed in the press-formed article; calculating a 4th order differential coefficient of the acquired cross section profile; and evaluating the line displacement, on the basis of the calculated 4th order differential coefficient of the cross section profile.

According to a second aspect of the invention based on the line displacement evaluation method of the first aspect, in the acquiring, a peak value H of the 4th order differential coefficient of the cross section profile on a side area of the character line where the line displacement occurs, and a displacement width L between a position where the peak value H appears and a position of an R stop of a design character line on the side area where the line displacement occurs may be determined, and the line displacement may be evaluated using the peak value H and the displacement width L.

According to a third aspect of the invention based on the line displacement evaluation method of the second aspect, in the acquiring, a first line displacement evaluation parameter S may be calculated from the following Formula (1), and the line displacement may be evaluated using the calculated first line displacement evaluation parameter S.

$$S = L \times |H|^n \quad (1)$$

Here, n is a weighting index that is determined in advance.

According to a fourth aspect of the invention based on the line displacement evaluation method of the second aspect, in the acquiring, a curve radius R of the character line may be further determined, and the line displacement may be evaluated using the peak value H, the displacement width L, and the curve radius R.

According to a fifth aspect of the invention based on the line displacement evaluation method of the fourth aspect, in the acquiring, a second line displacement evaluation parameter $S_{II}$ may be calculated from the following Formula (2), and the line displacement may be evaluated using the calculated second line displacement evaluation parameter $S_{II}$.

$$S_{II}=L\times(|H|/R)^m \tag{2}$$

Here, m is a weighting index that is determined in advance.

According to a sixth aspect of the invention, there is provided a line displacement evaluation device of evaluating line displacement occurring in a press-formed article in press forming of forming a character line. This device includes a cross sectional profile acquisition unit that acquires a cross section profile of the press-formed article measured so as to traverse the character line formed in the press-formed article; a 4th order differential coefficient calculation unit that calculates a 4th order differential coefficient of the cross section profile acquired in the cross section profile acquisition unit; and a line displacement evaluation parameter calculation unit that calculates a line displacement evaluation parameter for evaluating the line displacement, on the basis of the 4th order differential coefficient of the cross section profile calculated in the 4th order differential coefficient calculation unit.

A seventh aspect of the invention based on the line displacement evaluation device of the sixth aspect may further include a line displacement evaluation unit that evaluates the line displacement, on the basis of a line displacement evaluation parameter calculated in the line displacement evaluation parameter calculation unit.

According to an eighth aspect of the invention based on the line displacement evaluation device of the sixth or seventh aspect, the line displacement evaluation unit may determine a peak value H of the 4th order differential coefficient of the cross section profile on a side area of the character line where the line displacement occurs, and a displacement width L between a position where the peak value H appears and a position of an R stop of a design character line on the side area where the line displacement occurs, and may calculate the line displacement evaluation parameter using the peak value H and the displacement width L.

According to a ninth aspect of the invention based on the line displacement evaluation device of the eighth aspect, the evaluation parameter calculation unit may calculate a line displacement evaluation parameter S from the following Formula (1).

$$S=L\times|H|^n \tag{1}$$

Here, n is a weighting index that is determined in advance.

According to a tenth aspect of the invention based on the line displacement evaluation device of the eighth aspect, the evaluation parameter calculation unit may further determine a curve radius R of the character line, and calculates the line displacement evaluation parameter using the peak value H, the displacement width L, and the curve radius R.

According to an eleventh aspect of the invention based on the line displacement evaluation device of the tenth aspect, the evaluation parameter calculation unit may calculate a line displacement evaluation parameter $S_{II}$ from the following Formula (2).

$$S_{II}=L\times(|H|/R)^m \tag{2}$$

Here, m is a weighting index that is determined in advance.

According to a twelfth aspect of the invention, there is provided a program for evaluating line displacement occurring in a press-formed article in press forming of forming a character line. The program causes a computer to execute processing of acquiring a cross section profile of the press-formed article measured so as to traverse the character line formed in the press-formed article; processing of calculating a 4th order differential coefficient of the acquired cross section profile; and processing of calculating the line displacement evaluation parameter for evaluating the line displacement, on the basis of the calculated 4th order differential coefficient of the cross section profile.

A thirteenth aspect of the invention based on the program of the twelfth aspect may make the computer further execute processing of evaluating the line displacement, on the basis of the calculated line displacement evaluation parameter.

According to a fourteenth aspect of the invention based on the program of the twelfth or thirteenth aspect, in the processing of calculating the line displacement evaluation parameter, a peak value H of the 4th order differential coefficient of the cross section profile on a side area of the character line where the line displacement occurs, and a displacement width L between a position where the peak value H appears and a position of an R stop of a design character line on the side area where the line displacement occurs may be determined, and the line displacement evaluation parameter may be calculated using the peak value H and the displacement width L.

According to a fifteenth aspect of the invention based on the program of the fourteenth or thirteenth aspect, in the processing of calculating the line displacement evaluation parameter, the line displacement evaluation parameter S may be calculated from the following Formula (1).

$$S=L\times|H|^n \tag{1}$$

Here, n is a weighting index that is determined in advance.

According to a sixteenth aspect of the invention based on the program of the fourteenth aspect, in the processing of calculating the line displacement evaluation parameter, a curve radius R of the character line may be determined, and the line displacement evaluation parameter may be calculated using the peak value H, the displacement width L, and the curve radius R.

According to a seventeenth aspect of the invention based on the program of the sixteenth aspect, in the processing of calculating the line displacement evaluation parameter, the line displacement evaluation parameter $S_{II}$ may be calculated from the following Formula (2).

$$S_{II}=L\times(|H|/R)^m \tag{2}$$

Here, m is a weighting index that is determined in advance.

According to an eighteenth aspect of the invention, there is provided a computer-readable recording medium storing the program according to any one of the twelfth aspect to the seventeenth aspect.

Advantageous Effects of Invention

According to the invention, the line displacement occurring in the press-formed article can be quantitatively evaluated by using the line displacement evaluation parameter on the basis of the secondary differential coefficient of the curvature of the cross section profile, that is, the 4th order differential coefficient of the cross section profile, which constitutes the character line. Accordingly, stable product quality can be guaranteed.

DESCRIPTION OF EMBODIMENTS

Figure 1:
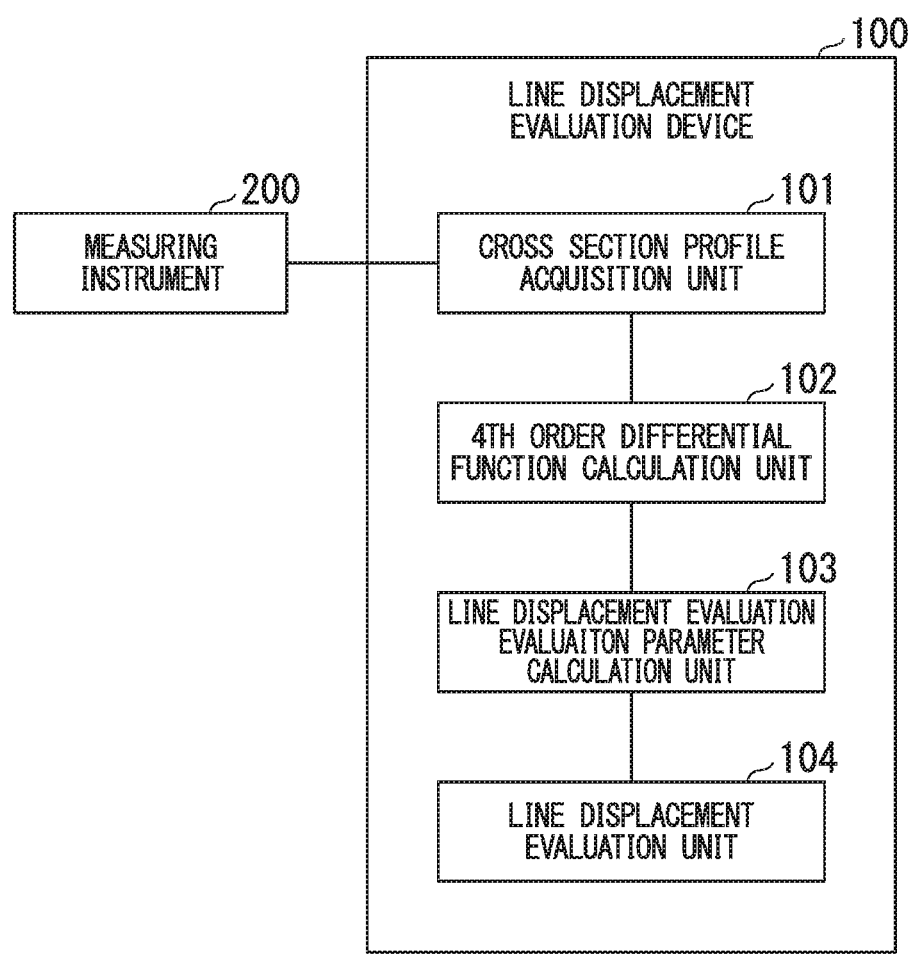
FIG. 1 is a view illustrating a functional configuration of a line displacement evaluation device related to an embodiment of the invention.

Hereinafter, a preferred embodiment of the invention will be described with reference to the accompanying drawings. A functional configuration of a line displacement evaluation device 100 related to an embodiment of the invention is illustrated in FIG. 1. The line displacement evaluation device 100 evaluates line displacement occurring in a press-formed article in press forming of forming a character line.

Figure 2A:
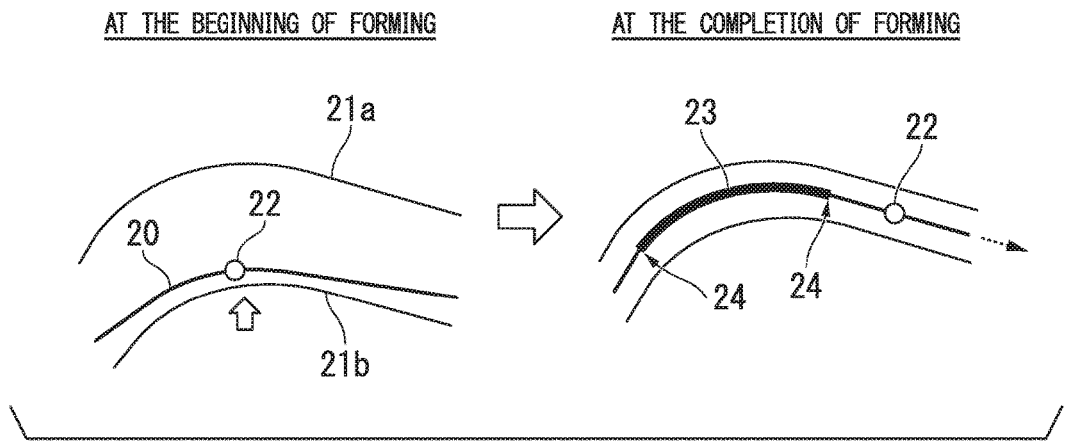
FIG. 2A is a view for explaining the outline of a line displacement phenomenon.
Figure 2B:
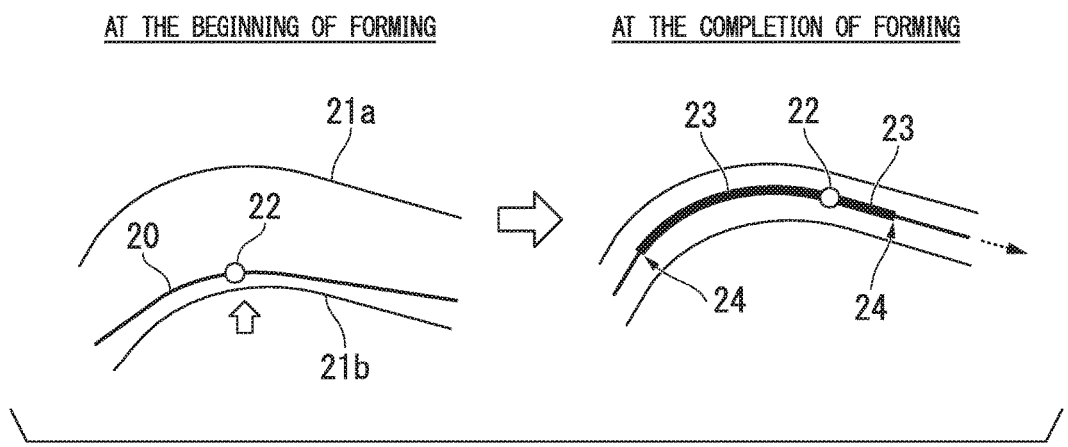
FIG. 2B is a view for explaining the outline of the line displacement phenomenon.

Here, the outline of a line displacement phenomenon occurring in the press-formed article in the press forming of forming a character line will be described with reference to FIGS. 2A and 2B. FIG. 2A is a view illustrating an example of forming (line displacement) in which a design property is impaired. FIG. 2B is a view illustrating an example of forming in which the design property is not impaired. In FIGS. 2A and 2B, a die consists of an upper die 21a and a lower die 21b, and a blank 20 is sandwiched and press-formed between the upper die 21a and the lower die 21b.

The blank 20 comes into contact with a design character line on the die during press forming (initial striking part 22). The initial striking part 22 moves (is displaced) as forming of a character line 23 proceeds, and a cross sectional shape different from a design at the time of designing is generated outside an R stop 24 of the character line 23. This is the line displacement phenomenon. The line displacement occurs when the initial striking part 22 between the blank and the die is displaced out of the R stop 24 of the character line 23 at of completion of press forming.

As in FIG. 2B, in a case where the initial striking part 22 between the blank and the die is inside the R stop 24 of the design character line 23 at the completion of press forming, the line displacement does not occur.

As illustrated in FIG. 1, the line displacement evaluation device 100 includes a cross section profile acquisition unit 101, a 4th order differential coefficient calculation unit 102, a line displacement evaluation parameter calculation unit 103, and a line displacement evaluation unit 104. In addition, the line displacement evaluation unit 104 may not be provided.

The cross section profile acquisition unit 101 acquires a cross section profile of the press-formed article measured by a profile measuring instrument 200 so as to traverse the character line formed in the press-formed article. Specifically, the cross section profile acquisition unit 101 acquires the cross section profile of the press-formed article, on the basis of profile data on a cross section orthogonal to the character line, from surface data on the press-formed article measured by the profile measuring instrument 200. Here, the "measuring so as to traverse the character line" means performing measurement of the press-formed article along a straight line (a straight line that forms a certain angle between 60° and 120° with respect to the character line) orthogonal to the character line.

Figure 3A:
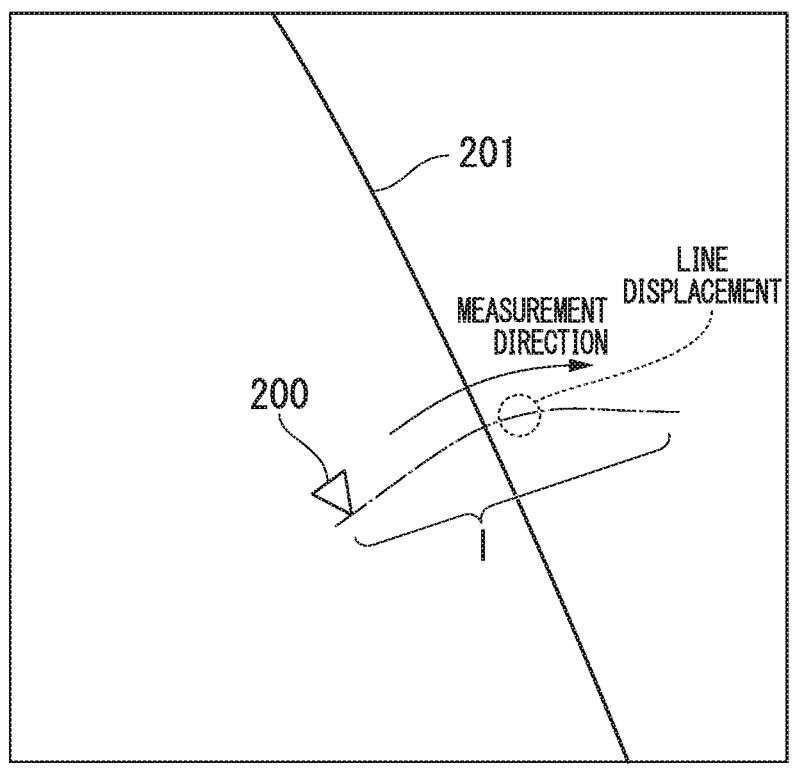
FIG. 3A is a view for explaining profile measurement of a press-formed article using a profile measuring instrument.

FIG. 3A is a view for explaining profile measurement of the press-formed article using the profile measuring instrument. In FIG. 3A, a contact type three-dimensional shape measuring instrument is used as an example of the profile measuring instrument 200. The profile measurement of the press-formed article is carried out with a predetermined measurement length l by moving the profile measuring instrument 200 in a direction in which the character line 201 is traversed, that is, in a direction orthogonal to the character line 201, while bridging the profile measuring instrument 200 into contact with the press-formed article. The line displacement occurs on any one side area of the character line 201. In the example of FIG. 3A, it is assumed that the line displacement occurs on the right side area of the character line 201 (a downstream side in a measurement direction by the profile measuring instrument) in the drawing.

In addition, if necessary, the profile measuring instrument 200 may perform profile measurement multiple times while changing its position in an extension direction of the character line 201 regarding one line displacement part.

In addition, a panel shape can be measured on a production line (in-line). Additionally, either one of a non-contact measuring instrument and a contact measuring instrument may be used. However, in a case where the degree of the line displacement is extremely minute, it is preferable to precisely measure the line displacement with the contact type measuring instrument.

It is preferable that the line displacement is evaluated in an assembled state actually in a product shipment state (finished body) and after the completion of press forming of the press-formed article. In a case where the press-formed article is evaluated before assembly and in a case where the surface rigidity of the press-formed article is low, deflection resulting from self-weight may occur depending on methods of setting the press-formed article at the time of measurement, a change may appear in the shape of a region where the line displacement occurs, and a profile measurement result may be different from that of a profile shape in a product shipment state (finished body).

The 4th order differential coefficient calculation unit 102 calculates the distribution of curvature (a secondary differential coefficient of the cross section profile), on the basis of the cross section profile acquired in the cross section profile acquisition unit 101, and calculates the secondary differential coefficient (a 4th order differential coefficient of the cross section profile) of the curvature. It is believed that the rate of change of the curvature or the secondary differential coefficient (the 4th order differential coefficient of the cross section profile) of the curvature has an influence on sensory evaluation of the line displacement, and the 4th order differential coefficient of the cross section profile is calculated.

Figure 3B:
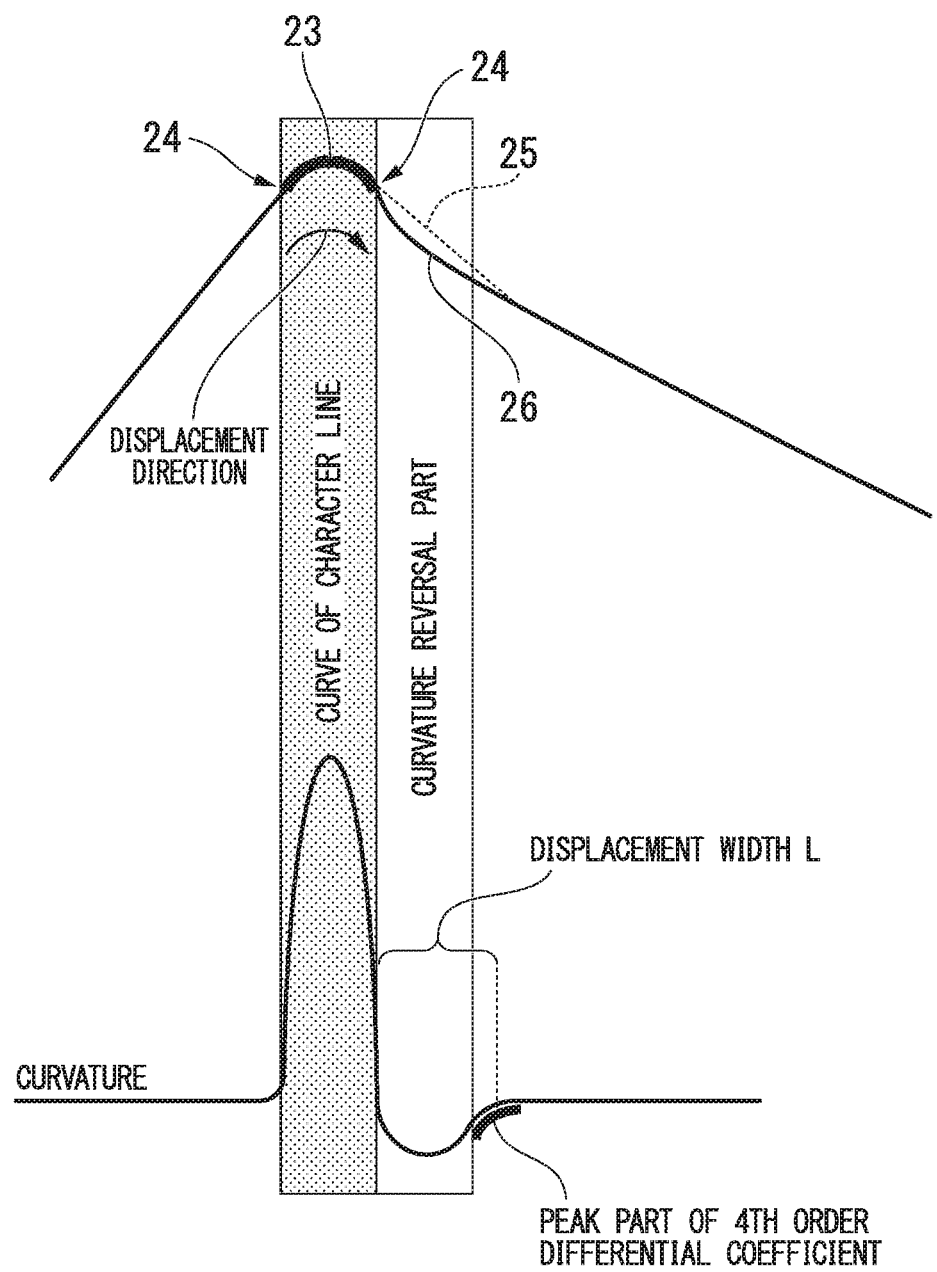
FIG. 3B is a view for explaining a relationship between a panel-shaped cross section of which the profile is measured, and curvature.

A relationship between the curvature and the line displacement will be described. An upper drawing of FIG. 3B is a view when the aspect of the line displacement is seen from the side. As illustrated in the upper drawing of FIG. 3B, a gap is made between a design shape 25 and an actual panel shape 26 outside the R stop 24 of the character line 23, and if this is seen from the surface of a panel, it can be seen that the line displacement appears.

In the region where the line displacement occurs, a curvature distribution in an opposite direction to a curvature distribution resulting from a curve of the design character line occurs (curvature reversal part). That is, the curvature is reversed in the region where line displacement occurs. In a region where the curvature is reversed, the shade of light is given, and the impression that the line displacement occurs is given to a confirmation worker.

In a case where a return way from the region where the curvature is reversed to an original shape is gentle in a region where the curvature on a side area where the line displacement occurs is reversed, a shade resulting from the line displacement is ambiguous seen. Therefore, the impression of the line displacement is small. On the other hand, in a case where the return way from the region where the curvature is reversed to the original shape is sharp, the shade resulting from the line displacement is emphasized. Therefore, the impression of the line displacement is great.

As a result of comparing a relationship between the sensory evaluation result of the line displacement and the curvature distribution on the side area where the line displacement occurs, it was ascertained that there is a correlation between the sensory evaluation result of the line displacement and the return way of the curvature distribution from the region where the curvature is reversed. The return way of the curvature distribution can be calculated from a secondary differential function (a 4th order differential function of the cross section profile) of the curvature distribution. Therefore, it is believed that the evaluation of the line displacement is allowed using a peak amount H of the secondary differential coefficient (the 4th order differential function of the cross section profile) of the curvature.

Figure 4:
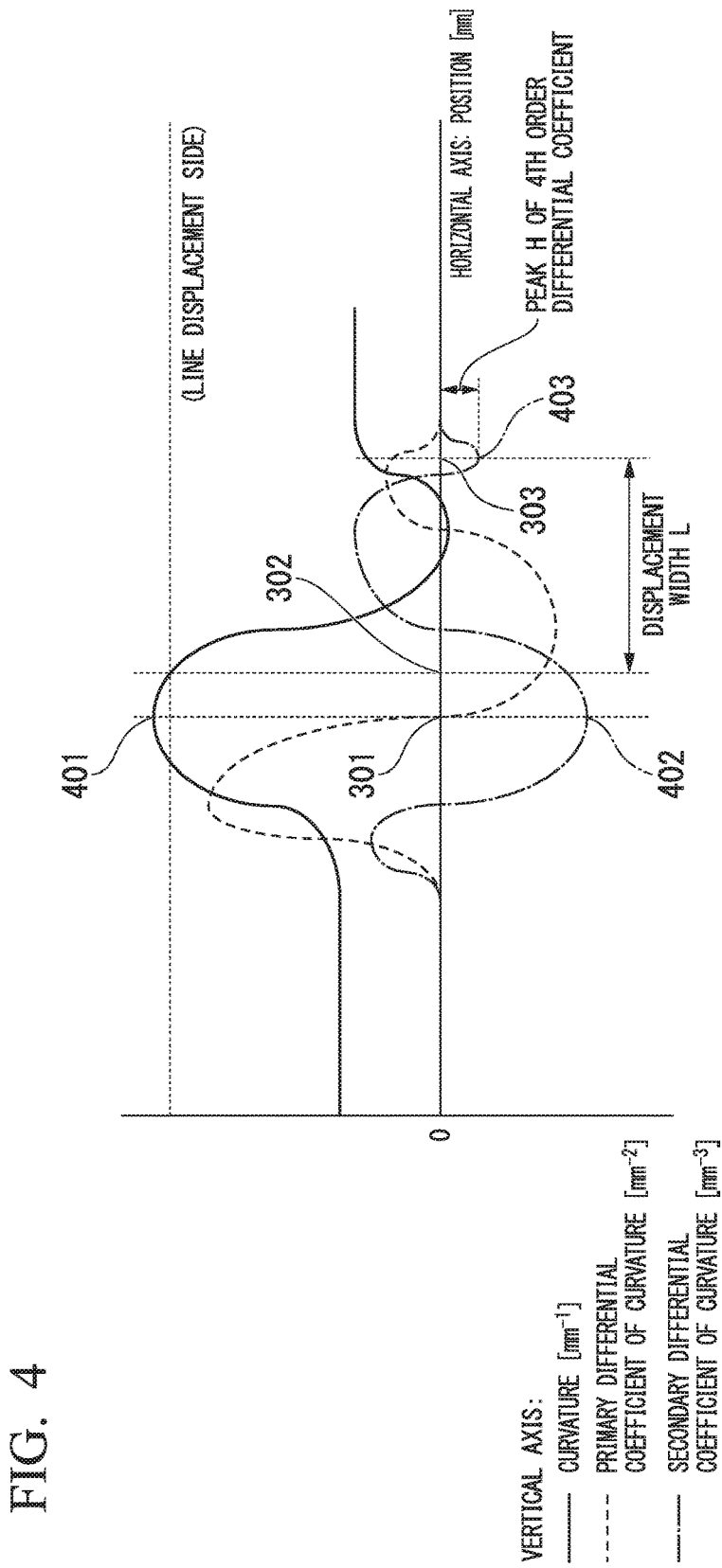
FIG. 4 is a view illustrating an example of curvature (a secondary differential coefficient of a cross section profile), a primary differential coefficient (a tertiary differential coefficient of the cross section profile) of the curvature, and a secondary differential coefficient (a 4th order differential coefficient of the cross section profile) of the curvature.

FIG. 4 is a view illustrating an example of the curvature (the secondary differential coefficient of the cross section profile) [mm$^{-1}$], a primary differential coefficient (a tertiary differential coefficient of the cross section profile) [mm$^{-2}$] of the curvature, and the secondary differential coefficient (the 4th order differential coefficient of the cross section profile) [mm$^{-3}$] of the curvature, which are calculated in the 4th order differential coefficient calculation unit 102. A vertical axis represents the curvature (the secondary differential coefficient of the cross section profile) [mm$^{-1}$], the primary differential coefficient (the tertiary differential coefficient of the cross section profile) [mm$^{-2}$] of the curvature, and the secondary differential coefficient (the 4th order differential coefficient of the cross section profile) [mm$^{-3}$] of the curvature. A horizontal axis represents the position, in a measurement direction (see FIG. 3A), of the profile by the profile measuring instrument.

As illustrated in FIG. 4, a peak 401 of the curvature appears at a position (the position of an R peak of the character line) 301 where a curve of the character line is the greatest. A peak 402 of the secondary differential coefficient (the 4th order differential coefficient of the cross section profile) of the curvature appears at the same position 301.

Figure 5:
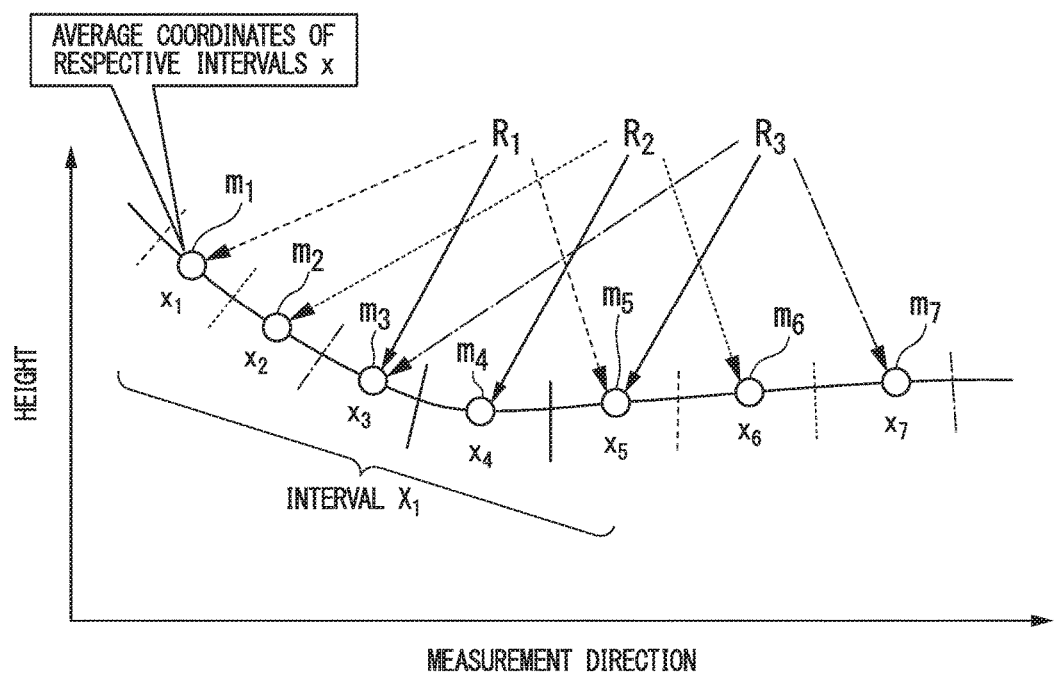
FIG. 5 is a view for explaining a method of calculating the distribution of curvatures.

A method of calculating calculates the distribution of the curvature using the 4th order differential coefficient calculation unit 102 will be described. FIG. 5 is a view for explaining the method of calculating the distribution of curvatures. A horizontal axis of FIG. 5 represents positions in the measurement direction, and a vertical axis represents positions in a height direction. A line on the drawing shows a cross section profile. When the distribution of the curvatures is calculated, as illustrated in FIG. 5, average coordinate points m ($m_1$, $m_2$, . . . ) are calculated in respective predetermined intervals x ($x_1$, $x_2$, . . . ) on the cross section profile. Then, circular arc radii R ($R_1$, $R_2$, . . . ) are calculated from three points ([$m_1$, $m_2$, and $m_3$ of FIG. 5) including both ends and a center of a curvature calculation interval X (in the example of FIG. 5, the curvature calculation interval X consists of five predetermined intervals $x_1$, $x_2$, $x_3$, $x_4$, and $x_5$) consisting of a plurality of predetermined intervals x, and curvatures that are inverse numbers of the circular arc radii are calculated. Next, predetermined intervals x to be starting points of the curvature calculation interval X are shifted to the next by 1 (the curvature calculation interval X consists of five predetermined intervals $x_2$, $x_3$, $x_4$, $x_5$, and $x_6$), circular arc radii R are calculated from three points ($m_2$, $m_3$, and $m_4$ of FIG. 5) including both ends and a center of the curvature calculation interval X, and curvatures that are inverse numbers of the circular arc radii are calculated. Subsequently, calculation of curvatures in the curvature calculation interval X is repeated while shifting predetermined intervals x to be starting points of a curvature calculation interval X to the next by 1. As the predetermined intervals, x, it is preferable to select that minimums of intervals that serve as sequence-of-points data that are as continuous as possible excluding noise when the distribution of curvatures are calculated.

The line displacement evaluation parameter calculation unit 103 calculates a line displacement evaluation parameter on the basis of the secondary differential coefficient (the 4th order differential function of the cross section profile) of the curvature calculated by the 4th order differential coefficient calculation unit 102. In a case where the line displacement occurs, as illustrated in FIG. 4, a peak 403 of the secondary differential coefficient (the 4th order differential function of the cross section profile) of the curvature appears on a side area of the character line where the line displacement occurs. Therefore, the line displacement evaluation parameter calculation unit 103 determines a value H [mm$^{-3}$] at the peak 403 of the secondary differential coefficient (the 4th order differential function of the cross section profile) of the curvature that appears on the side area where the line displacement occurs, and a displacement width L [mm] between a position 303 corresponding to the peak 403 and a position 302 of the R stop of the design character line. Then, the line displacement evaluation parameter calculation unit 103 calculates the line displacement evaluation parameter, on the basis of the value H and the displacement width L. For example, the line displacement evaluation parameter S is calculated from the following Formula (1).

$$\text{Line displacement evaluation parameter } S = L \times |H|^n \quad (1)$$

Here, n is a weighting index that is determined in advance.

The reason why the displacement width L is used is because it believed that the line displacement is a phenomenon in which the initial contact point of the die moves as illustrated in FIG. 2A and it is necessary to taken the movement distance of the initial contact point into consideration. In addition, in the present embodiment, a distance from the position 303 corresponding to the peak 403 of the secondary differential coefficient (the 4th order differential function of the cross section profile) of the curvature to the position 302 of the R stop of the design character line is defined as the displacement width L. However, a similar index may be used. For example, in a case where the size of a curve of a design character line seldom changes between panels to be compared with each other, or in a case where a distance from the position 301 of the R peak of the character line to the position 302 of the R stop of the design character line is small, a distance from the position 301 of the R peak of the design character line to the position 303 corresponding to the peak 403 of the secondary differential coefficient (the 4th order differential function of the cross section profile) of the curvature may be defined as the displacement width L.

Additionally, the reason why the value H of the peak of the secondary differential coefficient (the 4th order differential function of the cross section profile) of the curvature is used is because it is believed that the position of the peak of the curvature and the peak of the secondary differential coefficient (the 4th order differential function of the cross section profile) of the curvature are close to each other, and it is easy to catch a tendency.

The sensory evaluation receives the influence (corresponding to an absolute value of H) of a shade resulting from a change in the curvature on the side area where the line displacement occurs, and the influence (corresponding to the displacement width L) of the size of region where the line displacement occurs. As the absolute value of H is greater and L is greater, the line displacement is conspicuous and results of the sensory evaluation tend to become poor.

That is, it is preferable that, with an increase in the absolute value of H, the line displacement evaluation parameter S increases, and the calculation formula of the line displacement evaluation parameter S may have a form of addition or integration the absolute value of H, and L. Additionally, it is also possible to perform evaluation with any one of H and L. In this case, since a difference may appear in the sensory evaluation depending on the size of the other of H and L even if H and L are comparable with each other, it is preferable to use both H and L.

Although H is a minute value, a relative difference of H for each sample is greater compared to the displacement width L, and the relative difference can be reduced by n-th powering using the weighting index n. That is, the calculation formula of the line displacement evaluation parameter S becomes like Formula (1). In addition, in a case where n=⅓ is established, that is, in a case where $S=L\times|H|^{1/3}$ is used as the calculation formula of the line displacement evaluation parameter S, the present inventors have found out that a high correlation is shown between the sensory evaluation of the line displacement, and the line displacement evaluation parameter S.

In addition, in a case where the profile measurement is performed multiple times while changing positions in the extension direction of the character line with respect to one line displacement part as described above, for example, a value obtained by averaging line displacement evaluation parameters S calculated in the above respective times may be used as an index.

The line displacement evaluation unit 104 evaluates the line displacement on the basis of the line displacement evaluation parameter S calculated in the line displacement evaluation parameter calculation unit 103. As the line displacement evaluation parameter is greater, the line displacement is conspicuous, and as the line displacement evaluation parameter is smaller, the line displacement is not conspicuous. The evaluation of the line displacement may be performed while a human being refers to the line displacement evaluation parameter, or may be automated by a computer or the like.

Figure 6:
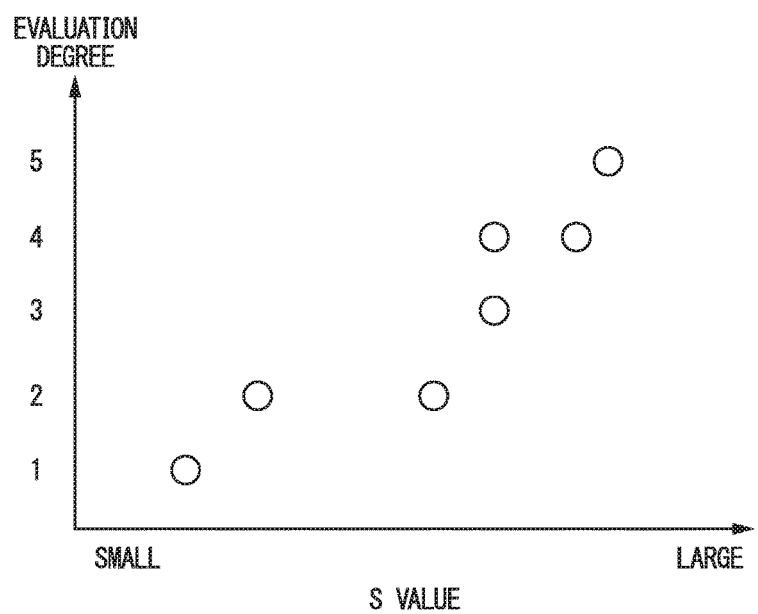
FIG. 6 is a view illustrating a relationship between a line displacement evaluation parameter S and the evaluation degree of sensory evaluation.

The invention was applied to an automobile outer panel where the line displacement occurs actually, the line displacement evaluation parameter S was calculated, and a correlation with the sensory evaluation was confirmed. FIG. 6 is a characteristic diagram illustrating a relationship between the line displacement evaluation parameter S and the evaluation degree of the sensory evaluation, in a case where $S=L\times|H|^{1/3}$ is used as a calculation formula of the line displacement evaluation parameter S. A horizontal axis of FIG. 6 represents the line displacement evaluation parameter S, and the line displacement evaluation parameter S becomes greater as it become closer to the right. A vertical axis of FIG. 6 represents the evaluation degree of the sensory evaluation, and the evaluation degree becomes greater as it moves upwards. This means that, as the evaluation degree is greater, the line displacement is conspicuous, and the evaluation degree is smaller, the line displacement is not conspicuous. A correlation in which, if the value of the line displacement evaluation parameter S became greater as illustrated in FIG. 6, the evaluation degree of the sensory evaluation became greater, was confirmed.

It is believed that that two factors of a cross sectional change factor determined depending on the strictness of a shape and a displacement width factor determined depending on a width in which the line displacement occurs are included in the sensory evaluation of the line displacement. Since the line displacement evaluation parameter S includes the value H of the peak of the secondary differential coefficient as the cross sectional change factor and includes the displacement width L as the displacement width factor and the tendencies of both can be ascertained, it can be said that this coincides with the sensory evaluation.

As described above, it can be seen that the line displacement can be quantitatively evaluated by the line displacement evaluation parameter S. If the line displacement can be quantitatively evaluated, stable product quality can be guaranteed.

As another embodiment, as a method of calculating the line displacement evaluation parameter, the radius R of a curve of a character line on the surface of a panel may be used in addition to the above-described value H and displacement width L. In a case where a difference is in the size of the radius R of a curve of a character line of a panel to be compared, there may be a correlation between the radius R of the curve of the character line and the line displacement sensory evaluation. In this case, as the radius R of the curve of the character line is greater, the sensory evaluation of the line displacement decreases, that is, there is a tendency in which the line displacement is not conspicuous. Thus, it is preferable that the line displacement evaluation parameter begins to decrease with an increase in the radius R of the curve of the character line. For example, the calculation formula of the line displacement evaluation parameter may have a form of subtraction or division of R. In addition, the radius of the curve of the design character line may be used as R. For example, the line displacement evaluation parameter $S_{II}$ is calculated from the following Formula (2).

$$\text{Line displacement evaluation parameter } S_{II}=L\times(|H|/R)^{m} \quad (2)$$

Here, m is a weighting index that is determined in advance.

Figure 7:
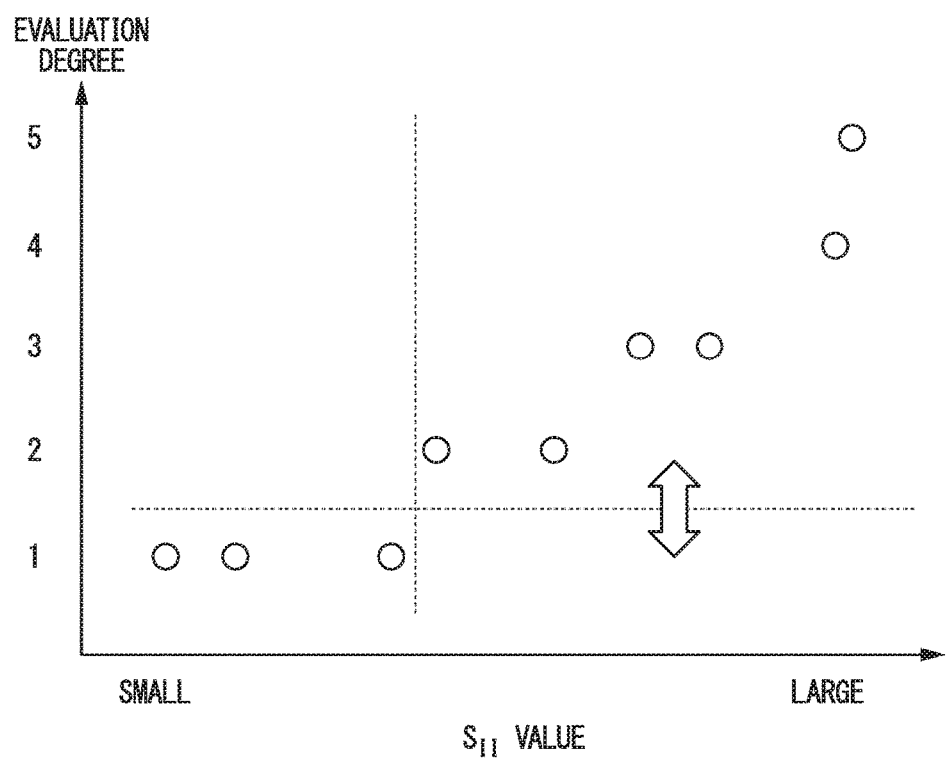
FIG. 7 is a view illustrating a relationship between a line displacement evaluation parameter $S_{II}$ and the evaluation degree of sensory evaluation.

In addition, in the present embodiment, in a case where m=⅕ is established, that is, in a case where $S_{II}=L\times(|H|/R)^{1/5}$ is used as the calculation formula of the line displacement evaluation parameter $S_{II}$, the present inventors have found out that a high correlation is shown between the sensory evaluation of the line displacement, and the line displacement evaluation parameter $S_{II}$. FIG. 7 is a characteristic diagram illustrating a relationship between the line displacement evaluation parameter $S_{II}$ and the evaluation degree of the sensory evaluation, in a case where $S_{II}=L\times(|H|/R)^{1/5}$ is used as a calculation formula of the line displacement evaluation parameter $S_{II}$. A horizontal axis of FIG. 7 represents the line displacement evaluation parameter $S_{II}$, and the line displacement evaluation parameter $S_{II}$ becomes greater as it become closer to the right. A vertical axis of FIG. 7 represents the evaluation degree of the sensory evaluation, and the evaluation degree becomes greater as it moves upwards. This means that, as the evaluation degree is greater, the line displacement is conspicuous, and the evaluation degree is smaller, the line displacement is not conspicuous. A correlation in which, if the value of the line displacement evaluation parameter $S_{II}$ became greater as illustrated in FIG. 7, the evaluation degree of the sensory evaluation became greater, was confirmed. Additionally, by using the line displacement evaluation parameter $S_{II}$, the effect that Evaluation Degree 1 and Evaluation Degree 2 were clearly distinguishable from each other was obtained.

In addition, in the above-described embodiment, a steel sheet is used as a plastically deformable sheet. However, as materials for the plastically deformable sheet, metallic materials, such as aluminum and titanium, glass-fibers strengthening resin materials, such as FRP and FRTP, and composite materials thereof may be used.

The line displacement evaluation device to which the invention is applied can be realized by, for example, a computer device including a CPU, a ROM, a RAM, and the like.

Additionally, the invention can also be realized by supplying software (program) realizing a line displacement evaluation function to a system or a device via a network or various storage media, and by readomg amd executing the program by the computer of the system or the device.

INDUSTRIAL APPLICABILITY

The invention can be widely applied to a method, a device, a program, and a recording medium that evaluate line displacement occurring in a press-formed article in press forming of forming a character line. Accordingly, the line displacement occurring in the press-formed article can be quantitatively evaluated, and stable product quality can be guaranteed.

REFERENCE SIGNS LIST

20: BLANK
21a: UPPER DIE
21b: LOWER DIE
22: INITIAL STRIKING PART
23: CHARACTER LINE
24: R STOP
25: DESIGN SHAPE
26: PANEL SHAPE
100: LINE DISPLACEMENT EVALUATION DEVICE
101: CROSS SECTION PROFILE ACQUISITION UNIT
102: 4TH ORDER DIFFERENTIAL COEFFICIENT CALCULATION UNIT
103: LINE DISPLACEMENT EVALUATION PARAMETER CALCULATION UNIT
104: LINE DISPLACEMENT EVALUATION UNIT
200 PROFILE MEASURING INSTRUMENT
201 CHARACTER LINE

The invention claimed is:

1. A line displacement evaluation method of evaluating line displacement occurring in a press-formed article in press forming of forming a character line, the method comprising:
acquiring a cross section profile of the press-formed article measured so as to traverse the character line formed in the press-formed article;
calculating a 4th order differential coefficient of the acquired cross section profile; and
evaluating the line displacement, on the basis of the calculated 4th order differential coefficient of the cross section profile,
wherein in the evaluating, a peak value H of the 4th order differential coefficient of the cross section profile on a side area of the character line where the line displacement occurs, and a displacement width L between a position where the peak value H appears and a position of an R stop of a design character line on the side area where the line displacement occurs are determined, and the line displacement is evaluated using the peak value H and the displacement width L, and
wherein in the evaluating a first line displacement evaluation parameter S is calculated from the following Formula (1), and the line displacement is evaluated using the calculated first line displacement evaluation parameter S, $$S=L\times|H|^{n} \quad (1)$$

here, n is a weighting index that is determined in advance.

2. The line displacement evaluation method according to claim 1, the method further comprising outputting the line displacement that was evaluated to determine the quality of the press-formed article.

3. A line displacement evaluation device of evaluating line displacement occurring in a press-formed article in press forming of forming a character line, the device comprising:
a cross sectional profile acquisition processing circuitry configured to acquire a cross section profile of the press-formed article measured so as to traverse the character line formed in the press-formed article;
a 4th order differential coefficient calculation processing circuitry configured to calculate a 4th order differential coefficient of the cross section profile acquired in the cross section profile acquisition processing circuitry;
a line displacement evaluation parameter calculation processing circuitry configured to calculate a line displacement evaluation parameter for evaluating the line displacement, on the basis of the 4th order differential coefficient of the cross section profile calculated in the 4th order differential coefficient calculation processing circuitry; and
a line displacement evaluation processing circuitry configured to evaluate the line displacement, on the basis of the line displacement evaluation parameter calculated in the line displacement evaluation parameter calculation processing circuitry, wherein the line displacement evaluation parameter calculation processing circuitry determines a peak value H of the 4th order differential coefficient of the cross section profile on a side area of the character line where the line displacement occurs, and a displacement width L between a position where the peak value H appears and a position of an R stop of a design character line on the side area where the line displacement occurs, and calculates the line displacement evaluation parameter using the peak value H and the displacement width L, wherein the line displacement evaluation parameter calculation processing circuitry calculates a line displacement evaluation parameter S from the following Formula (1), $$S = L \times |H|^n \qquad (1)$$

here, n is a weighting index that is determined in advance.

4. The line displacement evaluation device according to claim 3, wherein the line displacement evaluation processing circuitry outputs the line displacement that was evaluated to determine the quality of the press-formed article.

5. A non-transitory computer readable medium encoded with a computer program for evaluating line displacement occurring in a press-formed article in press forming of forming a character line, the program causing a computer to execute:

processing of acquiring a cross section profile of the press-formed article measured so as to traverse the character line formed in the press-formed article;

processing of calculating a 4th order differential coefficient of the acquired cross section profile;

processing of calculating the line displacement evaluation parameter for evaluating the line displacement, on the basis of the calculated 4th order differential coefficient of the cross section profile; and processing of evaluating the line displacement, on the basis of the calculated line displacement evaluation parameter, wherein in the processing of calculating the line displacement evaluation parameter, a peak value H of the 4th order differential coefficient of the cross section profile on a side area of the character line where the line displacement occurs, and a displacement width L between a position where the peak value H appears and a position of an R stop of a design character line on the side area where the line displacement occurs are determined, and the line displacement evaluation parameter is calculated using the peak value H and the displacement width L, and wherein in the processing of calculating the line displacement evaluation parameter, a line displacement evaluation parameter S is calculated from the following Formula (1), $$S = L \times |H|^n \qquad (1)$$

here, n is a weighting index that is determined in advance.

6. The non-transitory computer readable medium according to claim 5 encoded with a computer program for evaluating line displacement occurring in a press-formed article in press forming of forming a character line, the program causing a computer to further execute processing of outputting the line displacement that was evaluated to determine the quality of the press-formed article.

7. A line displacement evaluation method of evaluating line displacement occurring in a press-formed article in press forming of forming a character line, the method comprising:

acquiring a cross section profile of the press-formed article measured so as to traverse the character line formed in the press-formed article;

calculating a 4th order differential coefficient of the acquired cross section profile; and evaluating the line displacement, on the basis of the calculated 4th order differential coefficient of the cross section profile, wherein in the evaluating, a peak value H of the 4th order differential coefficient of the cross section profile on a side area of the character line where the line displacement occurs, and a displacement width L between a position where the peak value H appears and a position of an R stop of a design character line on the side area where the line displacement occurs are determined, and the line displacement is evaluated using the peak value H and the displacement width L, wherein in the evaluating, a curve radius R of the character line is further determined, and the line displacement is evaluated using the peak value H, the displacement width L, and the curve radius R, and a second line displacement evaluation parameter $S_{II}$ is calculated from the following Formula (2), and the line displacement is evaluated using the calculated second line displacement evaluation parameter $S_{II}$, $$S_{II} = L \times (|H|/R)^m \qquad (2)$$

Here, m is a weighting index that is determined in advance, and R is the curve radius.

8. The line displacement evaluation method according to claim 7, the method further comprising outputting the line displacement that was evaluated to determine the quality of the press-formed article.

9. A line displacement evaluation device of evaluating line displacement occurring in a press-formed article in press forming of forming a character line, the device comprising:

a cross sectional profile acquisition processing circuitry configured to acquire a cross section profile of the press-formed article measured so as to traverse the character line formed in the press-formed article;

a 4th order differential coefficient calculation processing circuitry configured to calculate a 4th order differential coefficient of the cross section profile acquired in the cross section profile acquisition processing circuitry;

a line displacement evaluation parameter calculation processing circuitry configured to calculate a line displacement evaluation parameter for evaluating the line displacement, on the basis of the 4th order differential coefficient of the cross section profile calculated in the 4th order differential coefficient calculation processing circuitry; and a line displacement evaluation processing circuitry configured to evaluate the line displacement, on the basis of the line displacement evaluation parameter calculated in the line displacement evaluation parameter calculation processing circuitry, wherein the line displacement evaluation parameter calculation processing circuitry determines a peak value H of the 4th order differential coefficient of the cross section profile on a side area of the character line where the line displacement occurs, and a displacement width L between a position where the peak value H appears and a position of an R stop of a design character line on the side area where the line displacement occurs, and calculates the line displacement evaluation parameter using the peak value H and the displacement width L, wherein the line displacement evaluation parameter calculation processing circuitry further determines a curve radius R of the character line, and calculates the line displacement evaluation parameter using the peak value H, the displacement width L, and the curve radius R, and wherein the line displacement evaluation parameter calculation processing circuitry calculates a line displacement evaluation parameter $S_{II}$ from the following Formula (2), $$S_{II} = L \times (|H|/R)^m \qquad (2)$$

Here, m is a weighting index that is determined in advance, and R is the curve radius.

10. The line displacement evaluation device according to claim 9, wherein the line displacement evaluation processing circuitry outputs the line displacement that was evaluated to determine the quality of the press-formed article.

11. A non-transitory computer readable medium encoded with a computer program for evaluating line displacement occurring in a press-formed article in press forming of forming a character line, the program causing a computer to execute:
   processing of acquiring a cross section profile of the press-formed article measured so as to traverse the character line formed in the press-formed article;
   processing of calculating a 4th order differential coefficient of the acquired cross section profile;
   processing of calculating the line displacement evaluation parameter for evaluating the line displacement, on the basis of the calculated 4th order differential coefficient of the cross section profile; and
   processing of evaluating the line displacement, on the basis of the calculated line displacement evaluation parameter, wherein in the processing of calculating the line displacement evaluation parameter, a peak value H of the 4th order differential coefficient of the cross section profile on a side area of the character line where the line displacement occurs, and a displacement width L between a position where the peak value H appears and a position of an R stop of a design character line on the side area where the line displacement occurs are determined, and the line displacement evaluation parameter is calculated using the peak value H and the displacement width L, wherein in the processing of calculating the line displacement evaluation parameter, a curve radius R of the character line is determined, and the line displacement evaluation parameter is calculated using the peak value H, the displacement width L, and the curve radius R, and wherein in the processing of calculating the line displacement evaluation parameter, a line displacement evaluation parameter $S_{II}$ is calculated from the following Formula (2), $$S_{II} = L \times (|H|/R)^m \qquad (2)$$

Here, m is a weighting index that is determined in advance, and R is the curve radius.

12. The non-transitory computer readable medium according to claim 11 encoded with a computer program for evaluating line displacement occurring in a press-formed article in press forming of forming a character line, the program causing a computer to further execute processing of outputting the line displacement that was evaluated to determine the quality of the press-formed article.

* * * * *